(12) United States Patent
Seibert et al.

(10) Patent No.: US 6,469,040 B2
(45) Date of Patent: *Oct. 22, 2002

(54) METHOD OF USING CYCLOOXYGENASE-2 INHIBITORS IN THE TREATMENT AND PREVENTION OF NEOPLASIA

(75) Inventors: Karen Seibert, St. Louis, MO (US); Jaime Masferrer, Ballwin, MO (US); Gary B Gordon, Highland Park, IL (US)

(73) Assignee: G.D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/862,128

(22) Filed: May 21, 2001

(65) Prior Publication Data

US 2001/0047024 A1 Nov. 29, 2001

Related U.S. Application Data

(63) Continuation of application No. 09/390,459, filed on Sep. 7, 1999, now abandoned, which is a continuation of application No. 08/949,922, filed on Oct. 14, 1997, now Pat. No. 5,972,986.

(51) Int. Cl.[7] ............................................. A61K 31/415
(52) U.S. Cl. ............................ 514/406; 514/8; 514/12; 514/210; 514/247; 514/252; 514/264; 514/271; 514/341; 514/365; 514/372; 514/374; 514/378; 514/399; 514/400; 514/403; 514/407; 514/602; 514/603; 514/604; 514/605; 514/709
(58) Field of Search ............................ 514/8, 12, 264, 514/271, 406, 210, 247, 252, 341, 365, 372, 374, 378, 399, 400, 403, 407, 602, 603, 604, 605, 709

(56) References Cited

U.S. PATENT DOCUMENTS 5,474,995 A * 12/1995 Ducharme et al. .......... 514/241
5,874,235 A *  2/1999 Chan et al. ................... 435/18

OTHER PUBLICATIONS

Huang et al, "Cyclooxygenase and 5–Lipoxygenase Inhibitors for the Prevention and Treatment of Cancer", Expert Opinion On Investigational Drugs, vol. 4, No. 3, pp. 243–249 (1995).*

* cited by examiner

*Primary Examiner*—Frederick Krass
(74) *Attorney, Agent, or Firm*—Banner & Witcoff, Ltd.

(57) ABSTRACT

This invention relates to the use of cyclooxygenase-2 inhibitors or derivatives thereof in preventing and treating neoplasia. In particular, the invention describes the method of preventing and treating epithelial cell neoplasia in a subject, said method comprising treating the subject with a therapeutically-effective amount of a compound of Formula I.

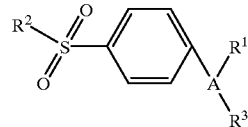

wherein A, $R^2$ and $R^3$ are as described in the specification.

12 Claims, No Drawings

METHOD OF USING CYCLOOXYGENASE-2 INHIBITORS IN THE TREATMENT AND PREVENTION OF NEOPLASIA

This is a continuation of application Ser. No. 09/390,459 filed Sep. 7, 1999 now abandoned which is a continuation of application Ser. No. 08/949,922 filed Oct. 14, 1997, now U.S. Pat. No. 5,772,986.

FIELD OF THE INVENTION

This invention is in the field of the prevention and treatment of neoplasia. More specifically, this invention relates to the use of cyclooxygenase-2 inhibitors or derivatives thereof in preventing and treating neoplasia.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAID's) that are active in reducing the prostaglandin-induced pain and swelling associated with the inflammation process are also active in affecting other prostaglandin-regulated processes not associated with the inflammation process. Thus, use of high doses of most common NSAID's can produce severe side effects, including life threatening ulcers, that limit their therapeutic potential. An alternative to NSAID's is the use of corticosteroids, which also produce adverse effects, especially when long term therapy is involved.

NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

Compounds which selectively inhibit cyclooxygenase-2 have been described in U.S. Pat. Nos. 5,380,738, 5,344,991, 5,393,790, 5,434,178, 5,474,995, 5,510,368 and WO documents WO96/06840, WO96/03388, WO96/03387, WO96/25405, WO95/15316, WO94/15932, WO94/27980, WO95/00501, WO94/13635, WO94/20480, and WO94/26731.

Neoplastic disease states are serious and oftentimes life-threatening conditions. These neoplastic diseases, which are characterized by rapidly-proliferating cell growth, continue to be the subject of worldwide research efforts directed toward the identification of therapeutic agents which are effective in the treatment thereof. Effective therapeutic agents prolong the survivability of the patient, inhibit the rapidly-proliferating cell growth associated with the neoplasm, or effect a regression of the neoplasm. Research in this area is primarily focused toward identifying agents which would be therapeutically effective in humans and other mammals.

Recently, the presence of COX-2 has been observed in neoplastic disease. See Masanobu Oshima et al. (Cell, 87, 803–809 (1996); and Michelle Parret et al. (International Journal of Oncology, 10, 503–507 (1997).

[Pyrazol-1-yl]benzenesulfonamides have been described as inhibitors of cyclooxygenase-2 and have shown promise in the treatment of inflammation, arthritis, and pain, with minimal side effects in pre-clinical and clinical trials. Their use for preventing colon cancer has been described in U.S. Pat. No. 5,466,823. However, their use for treating colon cancer or for treating or preventing other neoplasias has not been previously described.

The present invention is directed to the use of inhibitors of cyclooxygenase-2 for the treatment and prevention of neoplasias. Conjunctive treatment of a selective cyclooxygenase-2 inhibitor with other neoplastic agents produces a synergistic effect or alternatively reduces the toxic side effects associated with chemotherapy by reducing the concentration of the side effect-causing agent needed for therapeutic efficacy.

DETAILED DESCRIPTION OF THE INVENTION

The present invention provides a method for treating or preventing a neoplasia that produces a prostaglandin in a subject in need of such treatment or prevention, the method comprises treating the subject with a therapeutically effective amount of a cyclooxygenase-2 inhibitor or derivative thereof.

The term "treatment" includes partial or total inhibition of the neoplasia growth, spreading or metastasis, as well as partial or total destruction of the neoplasia cells.

The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia.

The phrase "therapeutically-effective" is intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or mammal subject who has any one of the known neoplasias, and preferably is a human subject. For methods of prevention, the subject is any human or animal subject, and preferably is a human subject who is at risk for obtaining an epithelium cell-derived neoplasia. The subject may be at risk due to exposure to carcinogenic agents, being genetically predisposed to have the neoplasia, and the like.

The term "neoplasia" includes neoplasia that produce prostaglandins or express a cyclooxygenase, including both benign and cancerous tumors, growths and polyps.

In the method above, the neoplasia that produce prostaglandins include brain cancer, bone cancer, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that effect epithelial cells throughout the body. Preferably, neoplasia is selected from gastrointestinal cancer, liver cancer, bladder cancer, pancreas cancer, ovary cancer, prostate cancer, cervical cancer, lung cancer, breast cancer and skin cancer, such as squamus cell and basal cell cancers. The COX-2 inhibitors can also be used to treat the fibrosis which occurs with radiation therapy. The method can be used to treat subjects having adenomatous polyps, including those with familial adenomatous polyposis (FAP). Additionally, the method can be used to prevent polyps from forming in patients at risk of FAP.

Inhibitors of the cyclooxygenase pathway in the metabolism of arachidonic acid used in the prevention and treatment of epithelial cell derived neoplasias may inhibit enzyme activity through a variety of mechanisms. By the way of example, the inhibitors used in the methods described herein may block the enzyme activity directly by acting as a substrate for the enzyme. The use of cyclooxygenasse-2 selective inhibitors is highly advantageous in that they minimize the gastric side effects that can occur with non-selective NSAID's, especially where prolonged prophylactic treatment is expected.

The term "cyclooxygenase-2 inhibitor" denotes a compound able to inhibit cyclooxygenase-2 without significant inhibition of cyclooxygenase-1. Preferably, it includes compounds which have a cyclooxygenase-2 $IC_{50}$ of less than about 0.2 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu$M, and more preferably of greater than 10 $\mu$M. Pyrazoles can be prepared by methods described in WO95/15316, WO95/15315 and WO96/03385. Thiophene analogs can be prepared by methods described in WO95/00501 and WO94/15932. Oxazoles can be prepared by the methods described in PCT documents WO95/00501 and WO94/27980. Isoxazoles can be prepared by the methods described in WO96/25405. Imidazoles can be prepared by the methods described in WO96/03388 and WO96/03387. Cyclopentene cyclooxygenase-2 inhibitors can be prepared by the methods described in U.S. Pat. No. 5,344,991 and WO 95/00501. Terphenyl compounds can be prepared by the methods described in WO96/16934. Thiazole compounds can be prepared by the methods described in WO96/03392. Pyridine compounds can be prepared by the methods described in WO96/24584 and WO96/24585.

The method provided herein relates to the use of cyclooxygenase-2 inhibitors or derivatives thereof in the prevention and treatment of derived neoplasias. In the preferred embodiments, the cycclooxygenase-2 compound is selected from the compounds of Formula I

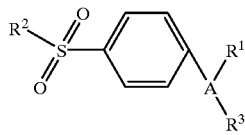

I wherein A is a substituent selected from partially unsaturated or unsaturated heterocyclyl and partially unsaturated or unsaturated carbocyclic rings;
wherein $R^1$ is at least one substituent selected from heterocyclyl, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;
wherein $R^2$ is methyl or amino; and
wherein $R^3$ is a radical selected from hydrido, halo, alkyl, alkenyl, alkynyl, oxo, cyano, carboxyl, cyanoalkyl, heterocyclyloxy, alkyloxy, alkylthio, alkylcarbonyl, cycloalkyl, aryl, haloalkyl, heterocyclyl, cycloalkenyl, aralkyl, heterocyclylalkyl, acyl, alkylthioalkyl, hydroxyalkyl, alkoxycarbonyl, arylcarbonyl, aralkylcarbonyl, aralkenyl, alkoxyalkyl, arylthioalkyl, aryloxyalkyl, aralkylthioalkyl, aralkoxyalkyl, alkoxyaralkoxyalkyl, alkoxycarbonylalkyl, aminocarbonyl, aminocarbonylalkyl, alkylaminocarbonyl, N-arylaminocarbonyl, N-alkyl-N-arylaminocarbonyl, alkylaminocarbonylalkyl, carboxyalkyl, alkylamino, N-arylamino, N-aralkylamino, N-alkyl-N-aralkylamino, N-alkyl-N-arylamino, aminoalkyl, alkylaminoalkyl, N-arylaminoalkyl, N-aralkylaminoalkyl, N-alkyl-N-aralkylaminoalkyl, N-alkyl-N-arylaminoalkyl, aryloxy, aralkoxy, arylthio, aralkylthio, alkylsulfinyl, alkylsulfonyl, aminosulfonyl, alkylaminosulfonyl, N-arylaminosulfonyl, arylsulfonyl, N-alkyl-N-arylaminosulfonyl; or a pharmaceutically-acceptable salt thereof.

A preferred class of compounds which inhibit cyclooxygenase-2 consists of compounds of Formula I wherein A is selected from 5- or 6-member partially unsaturated heterocyclyl, 5- or 6-member unsaturated heterocyclyl, 9- or 10-member unsaturated condensed heterocyclyl, lower cycloalkenyl and phenyl; wherein $R^1$ is selected from 5- and 6-membered heterocyclyl, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, lower alkoxyalkyl, lower alkylsulfinyl, halo, lower alkoxy and lower alkylthio; wherein $R^2$ is methyl or amino; and wherein $R^3$ is a radical selected from hydrido, oxo, cyano, carboxyl, lower alkoxycarbonyl, lower carboxyalkyl, lower cyanoalkyl, halo, lower alkyl, lower alkyloxy, lower cycloalkyl, phenyl, lower haloalkyl, 5- or 6-membered heterocyclyl, lower hydroxyalkyl, lower aralkyl, acyl, phenylcarbonyl, lower alkoxyalkyl, 5- or 6-membered heteroaryloxy, aminocarbonyl, lower alkylaminocarbonyl, lower alkylamino, lower aminoalkyl, lower alkylaminoalkyl, phenyloxy, and lower aralkoxy; or a pharmaceutically-acceptable salt thereof.

A more preferred class of compounds which inhibit cyclooxygenase-2 consists of compounds of Formula I wherein A is selected from oxazolyl, isoxazolyl, furyl, thienyl, dihydrofuryl, pyrrolyl, pyrazolyl, thiazolyl, imidazolyl, isothiazolyl, benzofuryl, cyclopentenyl, cyclopentadienyl, phenyl, and pyridyl; wherein $R^1$ is selected from pyridyl optionally substituted at a substitutable position with one or more methyl radicals, and phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, cyano, carboxyl, methoxycarbonyl, ethoxycarbonyl, hydroxyl, hydroxymethyl, trifluoromethoxy, amino, N-methylamino, N,N-dimethylamino, N-ethylamino, N,N-dipropylamino, N-butylamino, N-methyl-N-ethylamino, phenylamino, methoxymethyl, methylsulfinyl, fluoro, chloro, bromo, methoxy, ethoxy, propoxy, n-butoxy, pentoxy, and methylthio; wherein $R^2$ is methyl or amino; and wherein $R^3$ is a radical selected from hydrido, oxo, cyano, carboxyl, methoxycarbonyl, ethoxycarbonyl, carboxypropyl, carboxymethyl, carboxyethyl, cyanomethyl, fluoro, chloro, bromo, methyl, ethyl, isopropyl, butyl, tert-butyl, isobutyl, pentyl, hexyl, difluoromethyl, trifluoromethyl, pentafluoroethyl, heptafluoropropyl, difluoroethyl, difluoropropyl, methoxy, ethoxy, propoxy, n-butoxy, pentoxy, cyclohexyl, phenyl, pyridyl, thienyl, thiazolyl, oxazolyl, furyl, pyrazinyl, hydroxylmethyl, hydroxylpropyl, benzyl, formyl, phenylcarbonyl, methoxymethyl, furylmethyloxy, aminocarbonyl, N-methylaminocarbonyl, N,N-dimethylaminocarbonyl, N,N-dimethylamino, N-ethylamino, N,N-dipropylamino, N-butylamino, N-methyl-N-ethylamino, aminomethyl, N,N-dimethylaminomethyl, N-methyl-N-ethylaminomethyl, benzyloxy, and phenyloxy; or a pharmaceutically-acceptable salt thereof.

A family of specific compounds of particular interest within Formula I consists of compounds and pharmaceutically-acceptable salts thereof as follows:

5-(4-fluorophenyl)-1-[4-(methylsulfonyl)phenyl]-3-(trifluoromethyl)pyrazole;
4-(4-fluorophenyl)-5-[4-(methylsulfonyl)phenyl]-1-phenyl-3-(trifluoromethyl)pyrazole;
4-(5-(4-chlorophenyl)-3-(4-methoxyphenyl)-1H-pyrazol-1-yl)benzenesulfonamide
4-(3,5-bis(4-methylphenyl)-1H-pyrazol-1-yl)benzenesulfonamide;
4-(5-(4-chlorophenyl)-3-phenyl-1H-pyrazol-1-yl)benzenesulfonamide;
4-(3,5-bis(4-methoxyphenyl)-1H-pyrazol-1-yl)benzenesulfonamide;
4-(5-(4-chlorophenyl)-3-(4-methylphenyl)-1H-pyrazol-1-yl)benzenesulfonamide;
4-(5-(4-chlorophenyl)-3-(4-nitrophenyl)-1H-pyrazol-1-yl)benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl)benzenesulfonamide
4-[5-(4-chlorophenyl)-3-(trifluoromethyl)-1H-pyrazol-1-yl]benzenesulfonamide;
4-[5-phenyl-3-(trifluoromethyl)-1H-pyrazol-1-yl]benzenesulfonamide;
4-[5-(4-fluorophenyl)-3-(trifluoromethyl)-1H-pyrazol-1-yl]benzenesulfonamide;
4-[5-(4-methoxyphenyl)-3-(trifluoromethyl)-1H-pyrazol-1-yl]benzenesulfonamide;
4-[5-(4-chlorophenyl)-3-(difluoromethyl)-1H-pyrazol-1-yl]benzenesulfonamide;
4-[5-(4-methylphenyl)-3-(trifluoromethyl)-1H-pyrazol-1-yl]benzenesulfonamide;
4-[4-chloro-5-(4-chlorophenyl)-3-(trifluoromethyl)-1H-pyrazol-1-yl]benzenesulfonamide;
4-[3-(difluoromethyl)-5-(4-methylphenyl)-1H-pyrazol-1-yl]benzenesulfonamide;
4-[3-(difluoromethyl)-5-phenyl-1H-pyrazol-1-yl]benzenesulfonamide;
4-[3-(difluoromethyl)-5-(4-methoxyphenyl)-1H-pyrazol-1-yl]benzenesulfonamide;
4-[3-cyano-5-(4-fluorophenyl)-1H-pyrazol-1-yl]benzenesulfonamide;
4-[3-(difluoromethyl)-5-(3-fluoro-4-methoxyphenyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide;
4-[4-chloro-5-phenyl-1H-pyrazol-1-yl]benzenesulfonamide;
4-[5-(4-chlorophenyl)-3-(hydroxymethyl)-1H-pyrazol-1-yl]benzenesulfonamide;
4-[5-(4-(N,N-dimethylamino)phenyl)-3-(trifluoromethyl)-1H-pyrazol-1-yl]benzenesulfonamide;
5-(4-fluorophenyl)-6-[4-(methylsulfonyl)phenyl]spiro[2.4]hept-5-ene;
4-[6-(4-fluorophenyl)spiro[2.4]hept-5-en-5-yl]benzenesulfonamide;
6-(4-fluorophenyl)-7-[4-(methylsulfonyl)phenyl]spiro[3.4]oct-6-ene;
5-(3-chloro-4-methoxyphenyl)-6-[4-(methylsulfonyl)phenyl]spiro[2.4]hept-5-ene;
4-[6-(3-chloro-4-methoxyphenyl)spiro[2.4]hept-5-en-5-yl]benzenesulfonamide;
5-(3,5-dichloro-4-methoxyphenyl)-6-[4-(methylsulfonyl)phenyl]spiro[2.4]hept-5-ene;
5-(3-chloro-4-fluorophenyl)-6-[4-(methylsulfonyl)phenyl]spiro[2.4]hept-5-ene;
4-[6-(3,4-dichlorophenyl)spiro[2.4]hept-5-en-5-yl]benzenesulfonamide;
2-(3-chloro-4-fluorophenyl)-4-(4-fluorophenyl)-5-(4-methylsulfonylphenyl)thiazole;
2-(2-chlorophenyl)-4-(4-fluorophenyl)-5-(4-methylsulfonylphenyl)thiazole;
5-(4-fluorophenyl)-4-(4-methylsulfonylphenyl)-2-methylthiazole;
4-(4-fluorophenyl)-5-(4-methylsulfonylphenyl)-2-trifluoromethylthiazole;
4-(4-fluorophenyl)-5-(4-methylsulfonylphenyl)-2-(2-thienyl)thiazole;
4-(4-fluorophenyl)-5-(4-methylsulfonylphenyl)-2-benzylaminothiazole;
4-(4-fluorophenyl)-5-(4-methylsulfonylphenyl)-2-(1-propylamino)thiazole;
2-[(3,5-dichlorophenoxy)methyl]-4-(4-fluorophenyl)-5-[4-(methylsulfonyl)phenyl]thiazole;
5-(4-fluorophenyl)-4-(4-methylsulfonylphenyl)-2-trifluoromethylthiazole;
1-methylsulfonyl-4-[1,1-dimethyl-4-(4-fluorophenyl)cyclopenta-2,4-dien-3-yl]benzene;
4-[4-(4-fluorophenyl)-1,1-dimethylcyclopenta-2,4-dien-3-yl]benzenesulfonamide;
5-(4-fluorophenyl)-6-[4-(methylsulfonyl)phenyl]spiro[2.4]hepta-4,6-diene;
4-[6-(4-fluorophenyl)spiro[2.4]hepta-4,6-dien-5-yl]benzenesulfonamide;
6-(4-fluorophenyl)-2-methoxy-5-[4-(methylsulfonyl)phenyl]-pyridine-3-carbonitrile;
2-bromo-6-(4-fluorophenyl)-5-[4-(methylsulfonyl)phenyl]-pyridine-3-carbonitrile;
6-(4-fluorophenyl)-5-[4-(methylsulfonyl)phenyl]-2-phenyl-pyridine-3-carbonitrile;
4-[2-(4-methylpyridin-2-yl)-4-(trifluoromethyl)-1H-imidazol-1-yl]benzenesulfonamide;
4-[2-(5-methylpyridin-3-yl)-4-(trifluoromethyl)-1H-imidazol-1-yl]benzenesulfonamide;
4-[2-(2-methylpyridin-3-yl)-4-(trifluoromethyl)-1H-imidazol-1-yl]benzenesulfonamide;
3-[1-[4-(methylsulfonyl)phenyl]-4-(trifluoromethyl)-1H-imidazol-2-yl]pyridine;
2-[1-[4-(methylsulfonyl)phenyl-4-(trifluoromethyl)-1H-imidazol-2-yl]pyridine;
2-methyl-4-[1-[4-(methylsulfonyl)phenyl-4-(trifluoromethyl)-1H-imidazol-2-yl]pyridine;
2-methyl-6-[1-[4-(methylsulfonyl)phenyl-4-(trifluoromethyl)-1H-imidazol-2-yl]pyridine;
4-[2-(6-methylpyridin-3-yl)-4-(trifluoromethyl)-1H-imidazol-1-yl]benzenesulfonamide;
2-(3,4-difluorophenyl)-1-[4-(methylsulfonyl)phenyl]-4-(trifluoromethyl)-1H-imidazole;

4-[2-(4-methylphenyl)-4-(trifluoromethyl)-1H-imidazol-1-yl]benzenesulfonamide;
2-(4-chlorophenyl)-1-[4-(methylsulfonyl)phenyl]-4-methyl-1H-imidazole;
2-(4-chlorophenyl)-1-[4-(methylsulfonyl)phenyl]-4-phenyl-1H-imidazole;
2-(4-chlorophenyl)-4-(4-fluorophenyl)-1-[4-(methylsulfonyl)phenyl]-1H-imidazole;
2-(3-fluoro-4-methoxyphenyl)-1-[4-(methylsulfonyl)phenyl-4-(trifluoromethyl)-1H-imidazole;
1-[4-(methylsulfonyl)phenyl]-2-phenyl-4-trifluoromethyl-1H-imidazole;
2-(4-methylphenyl)-1-[4-(methylsulfonyl)phenyl]-4-trifluoromethyl-1H-imidazole;
4-[2-(3-chloro-4-methylphenyl)-4-(trifluoromethyl)-1H-imidazol-1-yl]benzenesulfonamide;
2-(3-fluoro-5-methylphenyl)-1-[4-(methylsulfonyl)phenyl]-4-(trifluoromethyl)-1H-imidazole;
4-[2-(3-fluoro-5-methylphenyl)-4-(trifluoromethyl)-1H-imidazol-1-yl]benzenesulfonamide;
2-(3-methylphenyl)-1-(4-(methylsulfonyl)phenyl]-4-trifluoromethyl-1H-imidazole;
4-[2-(3-methylphenyl)-4-trifluoromethyl-1H-imidazol-1-yl]benzenesulfonamide;
1-[4-(methylsulfonyl)phenyl]-2-(3-chlorophenyl)-4-trifluoromethyl-1H-imidazole;
4-[2-(3-chlorophenyl)-4-trifluoromethyl-1H-imidazol-1-yl]benzenesulfonamide;
4-[2-phenyl-4-trifluoromethyl-1H-imidazol-1-yl]benzenesulfonamide;
4-[2-(4-methoxy-3-chlorophenyl)-4-trifluoromethyl-1H-imidazol-1-yl]benzenesulfonamide;
1-allyl-4-(4-fluorophenyl)-3-[4-(methylsulfonyl)phenyl]-5-(trifluoromethyl)-1H-pyrazole;
4-[1-ethyl-4-(4-fluorophenyl)-5-(trifluoromethyl)-1H-pyrazol-3-yl]benzenesulfonamide;
N-phenyl-[4-(4-luorophenyl)-3-[4-(methylsulfonyl)phenyl]-5-(trifluoromethyl)-1H-pyrazol-1-yl]acetamide;
ethyl [4-(4-fluorophenyl)-3-[4-(methylsulfonyl)phenyl]-5-(trifluoromethyl)-1H-pyrazol-1-yl]acetate;
4-(4-fluorophenyl)-3-[4-(methylsulfonyl)phenyl]-1-(2-phenylethyl)-1H-pyrazole;
4-(4-fluorophenyl)-3-[4-(methylsulfonyl)phenyl]-1-(2-phenylethyl)-5-(trifluoromethyl)pyrazole;
1-ethyl-4-(4-fluorophenyl)-3-(4-(methylsulfonyl)phenyl]-5-(trifluoromethyl)-1H-pyrazole;
5-(4-fluorophenyl)-4-(4-methylsulfonylphenyl)-2-trifluoromethyl-1H-imidazole;
4-[4-(methylsulfonyl)phenyl]-5-(2-thiophenyl)-2-(trifluoromethyl)-1H-imidazole;
5-(4-fluorophenyl)-2-methoxy-4-[4-(methylsulfonyl)phenyl]-6-(trifluoromethyl)pyridine;
2-ethoxy-5-(4-fluorophenyl)-4-[4-(methylsulfonyl)phenyl]-6-(trifluoromethyl)pyridine;
5-(4-fluorophenyl)-4-[4-(methylsulfonyl)phenyl]-2-(2-propynyloxy)-6-(trifluoromethyl)pyridine;
2-bromo-5-(4-fluorophenyl)-4-[4-(methylsulfonyl)phenyl]-6-(trifluoromethyl)pyridine;
4-[2-(3-chloro-4-methoxyphenyl)-4,5-difluorophenyl]benzenesulfonamide;
1-(4-fluorophenyl)-2-[4-(methylsulfonyl)phenyl]benzene;
5-difluoromethyl-4-(4-methylsulfonylphenyl)-3-phenylisoxazole;
4-[3-ethyl-5-phenylisoxazol-4-yl]benzenesulfonamide;
4-[5-difluoromethyl-3-phenylisoxazol-4-yl]benzenesulfonamide;
4-[5-hydroxymethyl-3-phenylisoxazol-4-yl]benzenesulfonamide;
4-[5-methyl-3-phenyl-isoxazol-4-yl]benzenesulfonamide;
1-[2-(4-fluorophenyl)cyclopenten-1-yl]-4-(methylsulfonyl)benzene;
1-[2-(4-fluoro-2-methylphenyl)cyclopenten-1-yl]-4-(methylsulfonyl)benzene;
1-[2-(4-chlorophenyl)cyclopenten-1-yl]-4-(methylsulfonyl)benzene;
1-[2-(2,4-dichlorophenyl)cyclopenten-1-yl]-4-(methylsulfonyl)benzene;
1-[2-(4-trifluoromethylphenyl)cyclopenten-1-yl]-4-(methylsulfonyl)benzene;
1-[2-(4-methylthiophenyl)cyclopenten-1-yl]-4-(methylsulfonyl)benzene;
1-[2-(4-fluorophenyl)-4,4-dimethylcyclopenten-1-yl]-4-(methylsulfonyl)benzene;
4-[2-(4-fluorophenyl)-4,4-dimethylcyclopenten-1-yl]benzenesulfonamide;
1-[2-(4-chlorophenyl)-4,4-dimethylcyclopenten-1-yl]-4-(methylsulfonyl)benzene;
4-[2-(4-chlorophenyl)-4,4-dimethylcyclopenten-1-yl]benzenesulfonamide;
4-[2-(4-fluorophenyl)cyclopenten-1-yl]benzenesulfonamide;
4-[2-(4-chlorophenyl)cyclopenten-1-yl]benzenesulfonamide;
1-[2-(4-methoxyphenyl)cyclopenten-1-yl]-4-(methylsulfonyl)benzene;
1-[2-(2,3-difluorophenyl)cyclopenten-1-yl]-4-(methylsulfonyl)benzene;
4-[2-(3-fluoro-4-methoxyphenyl)cyclopenten-1-yl]benzenesulfonamide;
1-[2-(3-chloro-4-methoxyphenyl)cyclopenten-1-yl]-4-(methylsulfonyl)benzene;
4-[2-(3-chloro-4-fluorophenyl)cyclopenten-1-yl]benzenesulfonamide;
4-[2-(2-methylpyridin-5-yl)cyclopenten-1-yl]benzenesulfonamide;
ethyl 2-[4-(4-fluorophenyl)-5-[4-(methylsulfonyl)phenyl]oxazol-2-yl]-2-benzyl-acetate;
2-[4-(4-fluorophenyl)-5-[4-(methylsulfonyl)phenyl]oxazol-2-yl]acetic acid;
2-(tert-butyl)-4-(4-fluorophenyl)-5-[4-(methylsulfonyl)phenyl]oxazole;
4-(4-fluorophenyl)-5-[4-(methylsulfonyl)phenyl]-2-phenyloxazole;
4-(4-fluorophenyl)-2-methyl-5-[4-(methylsulfonyl)phenyl]oxazole; and
4-[5-(3-fluoro-4-methoxyphenyl)-2-trifluoromethyl-4-oxazolyl]benzenesulfonamide.

A family of specific compounds of more particular interest within Formula I consists of compounds and pharmaceutically-acceptable salts thereof as follows:

4-[5-(4-chlorophenyl)-3-(trifluoromethyl)-1H-pyrazol-1-yl]benzenesulfonamide;
4-[5-(4-methylphenyl)-3-(trifluoromethyl)-1H-pyrazol-1-yl]benzenesulfonamide;
4-[5-(3-fluoro-4-methoxyphenyl)-3-(difluoromethyl)-1H-pyrazol-1-yl]benzenesulfonamide;
3-[1-[4-(methylsulfonyl)phenyl]-4-trifluoromethyl-1H-imidazol-2-yl]pyridine;
2-methyl-5-[1-[4-(methylsulfonyl)phenyl]-4-trifluoromethyl-1H-imidazol-2-yl]pyridine;
4-[2-(5-methylpyridin-3-yl)-4-(trifluoromethyl)-1H-imidazol-1-yl]benzenesulfonamide;
4-[5-methyl-3-phenylisoxazol-4-yl]benzenesulfonamide;
4-[5-hydroxymethyl-3-phenylisoxazol-4-yl]benzenesulfonamide;

[2-trifluoromethyl-5-(3,4-difluorophenyl)-4-oxazolyl]
benzenesulfonamide;
4-[2-methyl-4-phenyl-5-oxazolyl]benzenesulfonamide; and
4-[5-(3-fluoro-4-methoxyphenyl-2-trifluoromethyl)-4-oxazolyl]benzenesulfonamide.

A subclass of cyclooxygenase-2 inhibitors is selected from compounds of WO95/15316. Preferably, the cyclooxygenase-2 inhibitor is selected from compounds of Formula II

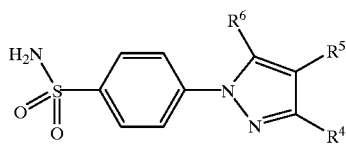

II wherein $R^4$ is lower haloalkyl; wherein $R^5$ is hydrido; and wherein $R^6$ is phenyl optionally substituted at a substitutable position with one or more radicals selected from halo, lower alkylthio, lower alkylsulfonyl, cyano, nitro, lower haloalkyl, lower alkyl, hydroxyl, lower alkenyl, lower hydroxyalkyl, carboxyl, lower cycloalkyl, lower alkylamino, lower dialkylamino, lower alkoxycarbonyl, aminocarbonyl, lower alkoxy, lower haloalkoxy, sulfamyl, five or six membered heterocyclic and amino; or a pharmaceutically-acceptable salt or derivative thereof.

A family of specific compounds of particular interest within Formula II consists of compounds, pharmaceutically-acceptable salts and derivatives thereof as follows:

4-[5-(4-chlorophenyl)-3-(trifluoromethyl)-1H-pyrazol-1-yl]
benzenesulfonamide;
4-[5-phenyl-3-(trifluoromethyl)-1H-pyrazol-1-yl]
benzenesulfonamide;
4-[5-(4-fluorophenyl)-3-(trifluoromethyl)-1H-pyrazol-1-yl]
benzenesulfonamide;
4-[5-(4-methoxyphenyl)-3-(trifluoromethyl)-1H-pyrazol-1-yl]benzenesulfonamide;
4-[5-(4-chlorophenyl)-3-(difluoromethyl)-1H-pyrazol-1-yl]
benzenesulfonamide;
4-[5-(4-methylphenyl)-3-(trifluoromethyl)-1H-pyrazol-1-yl]benzenesulfonamide;
4-[3-(difluoromethyl)-5-(4-methylphenyl)-1H-pyrazol-1-yl]
benzenesulfonamide;
4-[3-(difluoromethyl)-5-phenyl-1H-pyrazol-1-yl]
benzenesulfonamide;
4-[3-(difluoromethyl)-5-(4-methoxyphenyl)-1H-pyrazol-1-yl]benzenesulfonamide;
4-[3-(difluoromethyl)-5-(3-fluoro-4-methoxyphenyl)-1H-pyrazol-1-yl]benzenesulfonamide;
4-[5-(3-fluoro-4-methoxyphenyl)-3-(trifluoromethyl)-1H-pyrazol-1-yl]benzenesulfonamide; and
4-[5-(4-(N,N-dimethylamino)phenyl)-3-(trifluoromethyl)-1H-pyrazol-1-yl]benzenesulfonamide.

A family of specific compounds of more particular interest within Formula II consists of compounds and pharmaceutically-acceptable salts or derivatives thereof as follows:

4-[5-(4-methylphenyl)-3-(trifluoromethyl)-1H-pyrazol-1-yl]benzenesulfonamide;
4-[5-(4-chlorophenyl)-3-(difluoromethyl)-1H-pyrazol-1-yl]
benzenesulfonamide; and
4-[5-(3-fluoro-4-methoxyphenyl)-3-(difluoromethyl)-1H-pyrazol-1-yl]benzenesulfonamide.

Derivatives are intended to encompass any compounds which are structurally related to the cyclooxygenase-2 inhibitors or which possess the substantially equivalent biologic activity. By way of example, such inhibitors may include, but are not limited to, prodrugs thereof.

The compounds utilized in the methods of the present invention may be present in the form of free bases or pharmaceutically acceptable acid addition salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from chloroprocaine, choline, N,N'-dibenzylethylenediamine, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Biological Evaluation

The efficacy of cyclooxygenase-2 inhibitors as antineoplasia agents was determined in the following models:

Murine Lewis lung Carcinoma Model.

Lewis lung carcinomas were implanted sub-cutaneously into the foot pad of male C57BL/6 mice. The mice were subsequently treated with 4-[5-(4-chlorophenyl)-3-(difluoromethyl)-1H-pyrazol-1-yl]benzenesulfonamide. The drug was supplied in the drinking water at 6 mg/kg/day. Also a non-selective COX-1/COX-2 inhibitor indomethacin was tested in this model. The drug was supplied in the drinking water at the maximum tolerated dose of 2 mg/kg/day. A total of 10 mice/compound were tested. Tumor volume was determined twice a week using a plethysmometer. The efficacy of these compounds on tumor growth was measured at day 32 after cancer cell injection, as indicated in Table 1. The % inhibition value is calculated by calculating the difference in tumor size compared with the control group.

TABLE 1

| Tumor Volume (Day 32) | |
|---|---|
| Treatment | % Inhibition |
| Vehicle/control | 0.00 |
| COX-2 inhibitor | 70.86 |
| Indomethacin | 62.90 |

Human prostate cancer cell tumors

Two human prostate cancer cell lines (PC-3 and LNCaP) were obtained (ATCC) to determine the efficacy of cyclooxygenase-2 inhibitors to inhibit tumor growth in a therapeutic model. In addition, the LNCaP cell line secretes prostate serum antigen (PSA) when grown in nude mice.

PC-3

PC-3 cells ($10^6$ cells/0.2 ml of 30% matrigel) in RPMI 1640 medium was injected on the back of nude mice. At day 28, a COX-2 inhibitor 4-[5-(4-chlorophenyl)-3-(difluoromethyl)-1H-pyrazol-1-yl]benzenesulfonamide (20 mg/kg/day in water) was administered. After 45 days, $PGE_2$ and $TXB_2$ were measured. The COX-2 inhibitor inhibited tumor growth by 55%. $PGE_2$ and $TXB_2$ levels were reduced by 80–90% in the animals treated with the COX-2 inhibitor.

LNCaP

Similar to the results in PC-3, a COX-2 inhibitor 4-[5-(4-chlorophenyl)-3-(difluoromethyl)-1H-pyrazol-1-yl] benzenesulfonamide at a dose equivalent to 6 mg/kg/day in the drinking water inhibited the growth of the tumor by 55% at day 58. PSA level was reduced to approximately 50% as judged by western blotting.

Others

Cell lines: The following cell lines can be used: classic small cell lung cancer (SCLC) cell lines NCI-H209, NCI-H345, and NCI-H510; variant SCLC cell lines NCI-N417 and NCI-H82; large cell carcinoma cell line NCI-H1155; adeno carcinoma cell line NCI-H23; and bronchioalveolear carcinoma cell line A549, breast cancer cell line MCF-7 (American Type Tissue Culture Rockville MD; ATCC) and colon cancer cell lines such as NCI-H630 (ATCC), HT 29, SW948, HCA-7 and others that can be tested in vivo or in vitro. All cells can be grown in RPMI-1640, supplemented with 5% fetal bovine serum (FBS), penicillin and streptomycin (Gibco, Grand Island, N.Y.), and be maintained in a 5% $CO_2$ atmosphere at 37° C. All cell lines are free of mycoplasma contamination.

Growth studies: A modification (Promega CellTiter 96®, Promega Madison, Wis.) of the semiautomated colorimetric assay, MTT [Nakanishi, et al. *Exper. Cell Biol.*, 56, 74–85 (1988)], which quantitates cell numbers based on reduction of a tetrazolium compound by tumor cells as determined by a spectrophotometer (540 nm) is used. All assays are performed in RPMI-1640 media supplemented with transfertin ~10 g/ml, insulin ~5 g/ml and selenium (Sigma Chemicals, St. Louis, Mo.). Seeding densities are ~$2 \times 10^4$ cells/well, and cells are grown for 5 days. Each experiment is reported as mean optical density corrected for background +/− standard deviation. The cyclooxygenasse-2 inhibitors should be active, at a dose of 20 mg/kg, in inhibiting growth of the cancerous cell lines.

A mouse urinary bladder tumor model is performed with materials, reagents and procedures essentially as described by Grubbs et al, [*Anticancer Res.*, 13, 33–36 (1993)]. A COX-2 inhibitor should be active at a dose of 20 mg/kg.

A rat mammary tumor model is performed with materials, reagents and procedures essentially as described by Grubbs et al., [*Anticancer Res.*, 15, 709–16 (1995)]. A COX-2 inhibitor should be active at a dose of 20 mg/kg.

A mouse cervical and vaginal carcinogenesis model is performed with materials, reagents and procedures essentially as described by Arbeit et al., [*Proc. Acad. Sci. USA.*, 93, 2930–35 (1996)]. A COX-2 inhibitor should be active at a dose of 20 mg/kg.

A colon adenocarcinoma cell model is performed with materials, reagents and procedures essentially as described by Shiff et al., [*J. Clin. Invest.*, 96, 491–503 (1995)]. A COX-2 inhibitor should be active at a dose of 20 mg/kg. See also Masahiko Tsujii et al. (*Proc. Natl. Acad. Sci. USA* 94:3336-3340, 1997).

In summary, COX-2 inhibitors reduce tumor growth in several animal cancer models.

Combination Therapy of a COX-2 inhibitor and other antineoplastic agents

Lewis Lung carcinoma cells ($2.5 \times 10^6$ cells) prepared from a brei carried in C57BL/6 mice were injected subcutaneously into the hind legs of mice. A COX-2 inhibitor, 4-[5-(4-chlorophenyl)-3-(difluoromethyl)-1H-pyrazol-1-yl] benzenesulfonamide was given by gavage twice a week to groups of 10 mice at doses of 6 and 20 mg/kg. Cyclophosphamide (CTX) was injected to mice on days 5,7 and 9 after the implantation of the tumor at a dose of 50 mg/kg. Tumor volume was determined during the study. Animals were sacrificed at day 26 and the results of this experiments are summarized in Table 2. The % inhibition was calculated as above.

TABLE 2

| Treatment | Tumor Volume (Day 22) % Inhibition |
|---|---|
| Vehicle | 0 |
| COX-2 inhibitor (6 mg/kg) | 0 |
| COX-2 inhibitor (20 mg/kg) | 54 |
| CTX (50 mg/kg) | 57 |
| CTX + COX-2 inhibitor (6 mg/kg) | 69 |
| CTX + COX-2 inhibitor (20 mg/kg) | 77 |

The results of this experiment indicate that the combination of a COX-2 inhibitor and a cytotoxic agent produced an additive effect on their individual capacity to inhibit tumor growth.

The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intravascularly, intraperitoneally, intranasal, intrabronchial, subcutaneously, intramuscularly or topically (including aerosol).

The administration of the present invention may be for either prevention or treatment purposes. The methods and compositions used herein may be used alone or in conjunction with additional therapies known to those skilled in the art in the prevention or treatment of neoplasia. Alternatively, the methods and compositions described herein may be used as conjunctive therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases (MMP), SOD mimics or $\alpha_v\beta_3$ inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphirin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Examples of radioprotective agents which may be used in the combination chemotherapy of this invention are AD-5, adchnon, amifostine analogues, detox, dimesna, 1–102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

Methods for preparation of the antineoplastic agents described above may be found in the literature. Methods for preparation of doxorubicin, for example, are described in U.S. Pat. No. 3,590,028 and No. 4,012,448. Methods for preparing metallomatrix protease inhibitors are described in EP 780386. Methods for preparing SOD mimics are described in EP 524,101. Methods for preparing $\alpha_v\beta_3$ inhibitors are described in WO97/08174.

The phrase "conjunctive therapy" (or "combination therapy"), in defining use of a cyclooxygenase-2 inhibitor agent and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent. The present invention also comprises a pharmaceutical composition for the prevention and treatment of neoplasia, comprising a therapeutically-effective amount of a compound of Formula I in association with at least one pharmaceutically-acceptable carrier, adjuvant or diluent (collectively referred to herein as "carrier" materials) and, other antineoplastic agents or other growth inhibiting agents or other drugs or nutrients.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

If the neoplasia is localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol exipients, such as saline, and administered using commercially available nebulizers. Formulation in a fatty acid source may be used to enhance biocompatibility. Aerosol delivery is the preferred method of delivery for epithelial neoplasias of the lung for prevention application.

For rectal administration, the active ingredient may be formulated into suppositories using bases which are solid at room temperature and melt or dissolve at body temperature. Commonly used bases include cocoa butter, glycerinated gelatin, hydrogenated vegetable oil, polyethylene glycols of various molecular weights, and fatty esters of polyethylene stearate.

The dosage form and amount can be readily established by reference to known neoplasia treatment or prophylactic regiments. The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, the location of the neoplasia, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

All patents and documents referenced herein are incorporated by reference.

Although this invention has been described with respect to specific embodiments, the details of these embodiments are not to be construed as limitations.

What is claimed is:

1. A method of treating a neoplasia in a subject in need of such treatment, said method comprising treating the subject with a therapeutically-effective amount of a compound of Formula II

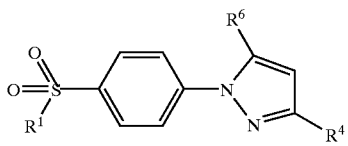

or a pharmaceutically acceptable salt thereof wherein
$R^1$ is methyl or amino;
$R^4$ is (i) $C_1$–$C_6$ haloalkyl, (ii) phenyl optionally substituted with one or more members independently selected from the group consisting of $C_1$–$C_6$ alkyl, $C_1$–$C_6$ alkoxy, nitro, cyano, halogen, hydroxy, amino, $C_1$–$C_6$ alkyl amino, and di-$C_1$–$C_6$ alkylamino groups, or (iii) thienyl optionally substituted with one or more members independently selected from the group consisting of $C_1$–$C_6$ alkyl, $C_1$–$C_6$ alkoxy, nitro, cyano, halogen, hydroxy, amino, $C_1$–$C_6$ alkylamino, and di($C_1$–$C_6$)alkylamino groups; and
$R^6$ is phenyl optionally substituted at a substitutable position with one or more radicals selected from the group consisting of halo, $C_1$–$C_6$ alkythio, $C_1$–$C_6$ alkylsulfonyl, cyano, nitro, $C_1$–$C_6$ haloalkyl, $C_1$–$C_6$ alkyl, hydroxyl, $C_1$–$C_6$ alkenyl, $C_1$–$C_6$ hydroxyalkyl, carboxyl, $C_1$–$C_6$ cycloalkyl, $C_1$–$C_6$ alkylamino, $C_1$–$C_6$ dialkylamino, $C_1$–$C_6$ alkoxycarbonyl, aminocarbonyl, $C_1$–$C_6$ alkoxy, $C_1$–$C_6$ haloalkoxy, sulfamyl, five or six membered heterocyclic radicals, and amino.

2. The method of claim 1 wherein the neoplasia is selected from the group consisting of colorectal cancer, gastrointestinal cancer, liver cancer, bladder cancer, cervical cancer, prostate cancer, lung cancer, breast cancer and skin cancer.

3. A method of claim 1, wherein the neoplasia is adenomatous polyps.

4. A method of treating a subject suffering from a neoplastic disease state with a conjunctive therapy, said method comprising treating the subject with a therapeutically-effective amount of a cyclooxygenase-2 selective compound and a compound selected from the group consisting of antibiotic agents, alkylating agents, antimetabolite agents, hormonal agents, immunological agents, interferon agents, metallomatrix proteases (MMP) inhibitors, SOD, and $\alpha_v\beta_3$ inhibitors, wherein the selective COX-2 inhibitor is a compound of formula II or formula III

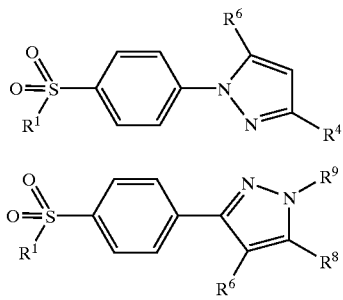

or a pharmaceutically acceptable salt thereof wherein
each $R^1$ is methyl or amino;
$R^4$ is (i) $C_1$–$C_6$ haloalkyl, (ii) phenyl optionally substituted with one or more members independently selected from the group consisting of $C_1$–$C_6$ alkyl, $C_1$–$C_6$ alkoxy, nitro, cyano, halogen, hydroxy, amino, $C_1$–$C_6$ alkyl amino, and di-$C_1$–$C_6$ alkylamino groups, or (iii) thienyl optionally substituted with one or more members independently selected from the group consisting of $C_1$–$C_6$ alkyl, $C_1$–$C_6$ alkoxy, nitro, cyano, halogen, hydroxy, amino $C_1$–$C_6$ alkylamino, and di($C_1$–$C_6$) alkylamino groups;
each $R^6$ is phenyl optionally substituted at a substitutable position with one or more radicals selected from the group consisting of halo, $C_1$–$C_6$ alkythio, $C_1$–$C_6$ alkylsulfonyl, cyano, nitro, $C_1$–$C_6$ haloalkyl, $C_1$–$C_6$ alkyl, hydroxyl, $C_1$–$C_6$ alkenyl, $C_1$–$C_6$ hydroxyalkyl, carboxyl, $C_1$–$C_6$ cycloalkyl, $C_1$–$C_6$ alkylamino, $C_1$–$C_6$ dialkylamino, $C_1$–$C_6$ alkoxycarbonyl, aminocarbonyl, $C_1$–$C_6$ alkoxy, $C_1$–$C_6$ haloalkoxy, sulfamyl, five or six membered heterocyclic radicals, and amino;
$R^8$ hydrogen or $C_1$–$C_6$ haloalkyl; and
$R^9$ is $C_1$–$C_6$ alkenyl, $C_1$–$C_6$ alkoxycarbonyl($C_1$–$C_2$) alkyl N-phenylacetamido, or phenyl($C_1$–$C_6$)alkyl.

5. The method of claim 4 wherein the compound is selected from compounds, and their pharmaceutically acceptable salts, of the group consisting of
5-(4-flurophenyl)-1-[4-(methysulfonyl)phenyl]-3-(trifluromethyl)pyrazole;
4-(4-flurophenyl)-5-[4-(methysulfonyl)phenyl]-1-phenyl-3-(trifluoromethyl)pyrazole;
4-(5-(4-chlorophenyl)-3-(4-methoxyphenyl)-1H-pyrazol-1-yl)benzenesulfonamide;
4-(3,5-bis(4-methyphenyl)-1H-pyrazol-1-yl)benzenesulfonamide;
4-(5-(4-chlorophenyl)-3-phenyl-1H-pyrazol-1-yl)benzenesulfonamide;
4-(3,5-bis(4-methoxyphenyl)-1H-pyrazol-1-yl)benzenesulfonamide;
4-(5-(4-chlorophenyl)-3-(4-methlphenyl)-1H-pyrazol-1-yl)benezenesulfonamide;
4-(5-(4-chlorophenyl)-3-(4-nitrophenyl)-1H-pyrazol-1-yl)benzenesulfonamide;
4-(5-(4-chlorophenyl)-3-(5-chloro-2-thienyl)-1H-pyrazol-1-yl)benzensulfonamide;
4-(4-chloro-3,5-diphenyl-1H-pyrazol-1-yl)benzenesulfonamide;
4-[4-chloro-5-(4-chlorophenyl)-3-(trifluoromethyl]-1H-pyrazol-1yl)benezensulfonamide;
4-[3-cyano-5-(4-fluorophenyl)-1H-pyrazol-1-yl]benzenesulfonamide;
4-[4-chloro-5-phenyl-1H-pyrazol-1-yl]benzenesulfonamide;
4-[(5-(4-chlorophenyl)-3-(hydroxymethyl)-1H-pyrazol-1-yl]benzenesulfonamide;
1-allyl-4-(4-flurophenyl)-3-(4-(methysulsonyl)phenyl)-5-(trifluoromethyl)-1H-pyrazole;
4-[1-ethyl-4-(4-fluorophenyl)-5-(trifluoromethyl)1H-pyrazol-3yl]benzenesulfonamide;
N-phenyl-[4-(4-fluorophenyl)-3-(4-(methyysulfonyl)phenyl)-5-(trifluromethyl)-1H-pyrazol-1yl]acetamide;
ethyl[4-(4-fluorophenyl)-3-(4-methysulfonyl)phenyl)-5-(trifluoromethyl)-1H-pyrazol-1-yl]acetate;
4-(4-fluorophenyl)-3-[4-methysulfonyl)phenyl]-1-(2-phenylethyl)-1H-pyrazole;
4-(4-fluorophenyl)-3-[4-methysulfonyl]phenyl)-1-(2-phenylethyl))-5-(trifluoromethyl)pyrazole; and
1-ethyl-4-(4-fluorophenyl)-3-(4-(methysulfonyl)phenyl)-5-(trifluoromethyl)-1H-pyrazole.

6. The method of claim 5 wherein the compound is selected from compounds, and their pharmaceutically acceptable salts, of the group consisting of
4-[5-(4-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide; and
4-[5-(3-fluoro-4-methoxyphenyl)-3-(difluoromethyl)-1H-pyrazol-1-yl]benzenesulfonamide.

7. A method of treating a neoplasia in a subject in need of such treatment, said method comprising treating the subject with a therapeutically-effective amount of a compound of the formula

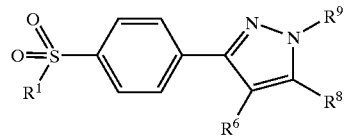

or a pharmaceutically acceptable salt thereof wherein
$R^1$ is methyl or amino;
$R^6$ is phenyl optionally substituted at a substitutable position with one or more radicals selected from the group consisting of halo, $C_1-C_6$ alkylthio, $C_1-C_6$ alkylsulfonyl, cyano, nitro, $C_1-C_6$ haloalkyl, $C_1-C_6$ alkyl, hydroxyl, $C_1-C_6$ alkenyl, $C_1-C_6$ hydroxyalkyl, carboxyl, $C_1-C_6$ cyloalalkyl, $C_1-C_6$ alkylamico, $C_1-C_6$ dialkylamino, $C_1-C_6$ alkoxycarbonyl, aminocarbonyl, $C_1-C_6$ alkoxy, $C_1-C_6$ haloalkoxy, sulfamyl, five or six membered heterocyclic radicals, and amino;
$R^8$ is hydrogen or $C_1-C_6$ hyloalkyl; and
$R^9$ $C_1-C_6$ alkyl, $C_2-C_6$ alkenyl, $C_1-C_6$ alkoxycarbonyl $(C_1-C_2)$ alkyl, N-phenylacetamido, or phenyl $(C_1-C_6)$ alkyl.

8. The method of claim 7 wherein the compound is selected from compounds, and their pharmaceutically acceptable salts, of the group consisting of
5-(4-fluorophenyl)-1-4-(methylsulfonyl)phenyl)-3-(trifluoromethyl)pyrazole;
4-(4-fluorophenyl)-5-4-(methylsulfonyl)phenyl)-1-phenyl-3-(trifluoromethyl)pyrazole;
4-(5-(4-chlorophenyl)-3-(4-methoxyphenyl)-1H-pyrazol-1-yl)benzenesulfonamide;
4-(3,5-bis(4-methylphenyl)-1H-pyrazol-1-yl)benzenesulfonamide;
4-(5-(4-chlorophenyl)-3-phenyl-1H-pyrazol-1-yl)benzenesulfonamide;
4-(3,5-bis(4-methoxyphenyl)-1H-pyrazol-1-yl)benzenesulfonamide;
4-(5-(4-chlorophenyl)-3-(4-methylphenyl)-1H-pyrazol-1-pyrazol)benzenesulfonamide;
4-(5-(4-chlorophenyl)-3-(4-nitrophenyl)-1H-pyrazol-1yl)benzenesulfonamide;
4-(5-(4-chlorophenyl)-3-(5-chloro-2-thienyl)-1H-pyrazol-1-yl)benzenesulfonamide;
4-(4-chloro-3,5-diphenyl-1H-pyrazol-1-yl)benzenesulfonamide;
4-[4-chloro-5-(4-chlorophenyl)-3-(trifluoromethyl)-1H-pyrazol-1-yl]benzenesulfonamide;
4-[3-cyano-5-(4-fluorophenyl)-1H-pyrazol-1-yl]benzenesulfonamide;
4-[4-chloro-5-phenyl-1H-pyrazol-1-yl]benzenesulfonamide; and
4-[(5-(4-chlorophenyl)-3-(hydroxymethyl)-1H-pyrazol-1-yl]benzenesulfonamide.

9. The method of claim 7 wherein the compound is selected from compounds, and their pharmaceutically acceptable salts, of the group consisting of
1-allyl-4-(4-fluorophenyl)-3-[4-(methysulfonyl)phenyl]-5-(trifluoromethyl)-1H-pyrazole;
4-[1-ethyl-4-(4-fluorophenyl)-5-(trifluoromethyl)-1H-pyrazol-3-yl]benzenesulfonamide;
N-phenyl-4-(4-fluorophenyl)-3-[4-(methylsulfonyl)phenyl-5-(trifluromethyl)-1H-pyrazol-1-yl]acetamide;
ethyl4-(4-fluorophenyl)-3-[4-(methylsulfonyl)phenyl-5-(trifluoromethyl)-1H-pyrazol-1-yl]acetate;
4-(4-fluorophenyl)-3-4-[(methylsulfonyl)phenyl]-1-(2-phenylethyl)-1H-pyrazole;
4-(4-fluorophenyl)-3-[4-(methylsulfonyl)phenyl]-1-(2-phenylethyl)-5-(trifluoromethyl)pyrazole; and
1-ethyl-4-(4-fluorophenyl)-3-[4-(methylsulfonyl)phenyl]-5-(trifluoromethyl)-1H-pyrazole.

10. A method of treating familial adenomatous polyps in a subject in need of such treatment, said method comprising administering to the subject a therepeutically-effective amount of a compound which is 4-5-(4-methylphenyl)-3-(trifluoromethyl)-1H-pyrazol-1-yl)benzenesulfonamide.

11. A method of treating familial adenomatous polyps in a subject in need of such treatment, said method comprising admistering to the subject a pharmaceutical composition comprising 4-5-(4-methylphenyl)-3-(trifluoromethyl)-1H-pyrazol-1-yl)benzenesulfonamide together with a pharmaceutically acceptable carrier.

12. A method according to claim 11, wherein the carrier comprises lactose, magnesium stearate, and gelatin.

* * * * *